(12) United States Patent
Vaughn et al.

(10) Patent No.: US 8,080,700 B2
(45) Date of Patent: Dec. 20, 2011

(54) SYSTEM AND METHOD FOR REDUCING DECOMPOSITION BYPRODUCTS IN A METHANOL TO OLEFIN REACTOR SYSTEM

(75) Inventors: Stephen N. Vaughn, Kingwood, TX (US); Gary T. Schmidt, Kingwood, TX (US); Teng Xu, Hampton, NJ (US); Christopher E. Dilley, Sugar Land, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 488 days.

(21) Appl. No.: 12/334,967

(22) Filed: Dec. 15, 2008

(65) Prior Publication Data

US 2010/0152513 A1 Jun. 17, 2010

(51) Int. Cl.
*C07C 1/00* (2006.01)
*B01J 19/00* (2006.01)

(52) U.S. Cl. ........ 585/636; 585/638; 585/639; 585/640; 585/920; 585/923; 502/65; 422/219

(58) Field of Classification Search ............... 585/636, 585/638, 639, 640, 920, 923; 502/65; 422/219
See application file for complete search history.

(56) References Cited

U.S. PATENT DOCUMENTS

| | | | |
|---|---|---|---|
| 5,367,100 A * | 11/1994 | Gongwei et al. | 585/640 |
| 6,737,556 B2 | 5/2004 | Jones et al. | |
| 6,844,291 B2 | 1/2005 | Levin et al. | |
| 7,034,196 B2 | 4/2006 | Clem et al. | |
| 7,067,108 B2 | 6/2006 | Mertens et al. | |
| 7,208,442 B2 | 4/2007 | Xu et al. | |
| 7,338,645 B2 | 3/2008 | Jones et al. | |
| 2006/0020155 A1 * | 1/2006 | Beech et al. | 585/639 |

FOREIGN PATENT DOCUMENTS

| | | |
|---|---|---|
| EP | 0 249 915 | 12/1987 |
| JP | 01090136 | 4/1989 |
| WO | WO 9829370 | 7/1998 |

* cited by examiner

*Primary Examiner* — Prem C Singh
(74) *Attorney, Agent, or Firm* — Kevin M. Faulkner; Gerald J. Hughes

(57) ABSTRACT

The invention relates to a method for forming olefins from an oxygenate-containing feedstock, comprising contacting the at least partially vaporized feed comprising oxygenates with a first catalyst upstream of an OTO reactor, the first catalyst consisting of a reactive guard bed of metal oxides comprising one or more metals from Groups 2, 3, and 4 of the Periodic Table and/or one or more metals in the Lanthanide and Actinide series, then contacting the feedstock in the OTO reactor with a second catalyst under conditions effective to form an effluent comprising the olefins.

20 Claims, 1 Drawing Sheet

SYSTEM AND METHOD FOR REDUCING DECOMPOSITION BYPRODUCTS IN A METHANOL TO OLEFIN REACTOR SYSTEM

FIELD OF THE INVENTION

This invention relates to a system and method for reducing methanol decomposition byproducts in a methanol to olefin reactor system.

BACKGROUND OF THE INVENTION

Light olefins, defined herein as ethylene and propylene, serve as feeds for the production of numerous important chemicals and polymers. Light olefins traditionally are produced by cracking petroleum feeds. The escalating cost of petroleum feeds has led to the development of new technology for producing light olefins, such as oxygenate-to-olefin ("OTO") technology.

In an OTO reaction system, a feedstock containing an oxygenate is vaporized and introduced into a reactor. Exemplary oxygenates include alcohols such as methanol and ethanol, dimethyl ether, methyl ethyl ether, methyl formate, and dimethyl carbonate. In a methanol to olefin (MTO) reaction system, the oxygenate-containing feedstock includes methanol. In the reactor, the methanol contacts a catalyst under conditions effective to create desirable light olefins. Typically, molecular sieve catalysts have been used to convert oxygenate compounds to olefins. Silicoaluminophosphate (SAPO) molecular sieve catalysts are particularly desirable in such conversion processes because they are highly selective in the formation of ethylene and propylene.

MTO reactor systems can form undesirable byproducts through side reactions. For example, the metals in conventional reactor walls may act as catalysts in one or more side reactions. If the methanol contacts the metal reactor wall at sufficient temperature and pressure, the methanol may be converted to undesirable methane and/or other byproducts. Byproduct formation in an MTO reactor is undesirable for several reasons. First, increased investment is required to separate and recover the byproducts from the desired light olefins. Additionally, consuming feed in byproduct reactions results in less feed being available for the desired light olefins, thereby reducing light olefin yield. While the relative concentration of metal-catalyzed side reaction byproducts is generally quite low, the total amount of byproducts produced on an industrial scale can be very large. Thus, it is desirable to decrease or the amount of byproducts produced by an MTO reactor system. One way to do this is by deactivating or passivating reactor surfaces.

Sulfur-containing chemicals have proven effective for deactivating or passivating the metal surface of a reactor thereby reducing the formation of undesirable byproducts in the reactor. For example, Japanese Laid Open Patent Application JP 01090136 to Yoshinari, et al. is directed to a method for preventing decomposition of methanol or dimethyl ether and coking by sulfiding the metal surface of a reactor. More particularly, the method includes reacting methanol and/or dimethyl ether in the presence of a catalyst at above 450° C. in a tubular reactor made of Iron and/or Nickel or stainless steel. The inside wall of the reactor is sulfided with a compound such as carbon disulfide, hydrogen disulfide or dimethyl sulfide. Additionally, a sulphur compound may be added to the feed.

Byproduct production can also be curtailed by reducing the amount of feed decomposition in the MTO reaction system's feed vaporization and injection region. For example, U.S. Pat. No. 7,034,196, discloses a method for reducing methanol decomposition by regulating the temperature of the feed injectors. Other references, such as U.S. Pat. Nos. 7,338,645 and 6,737,556, disclose coating a portion of the feed injectors with materials that are not catalytically active for methanol decomposition.

While these methods have proven effective, further reductions in the amount of methanol feed decomposition and/or the conversion to undesirable byproducts are desired.

SUMMARY OF THE INVENTION

In an embodiment, the invention relates to a method for forming light-olefins from an oxygenate-containing feedstock, comprising:
contacting the feedstock with a first catalyst upstream of an OTO reactor, the first catalyst comprising one or more metals from Groups 2, 3, and 4 of the Periodic Table and/or one or more metals in the Lanthanide and Actinide series; and then
contacting, in the OTO reactor, the feedstock with a second catalyst under conditions effective to form an effluent comprising the light olefins.

In another embodiment, the invention relates to a feed vaporization and introduction system for an OTO reactor, comprising:
means for vaporizing at least a portion of the feed;
means for contacting the at least partially vaporized feed with a first catalyst comprising one or more metals from Groups 2, 3, and 4 of the Periodic Table and/or one or more metals in the Lanthanide and Actinide series; and
a feed introduction means downstream of the contacting means, the feed introduction means comprising a first generally tubular member having a first end for receiving the at least partially vaporized feed, a second end adjacent to the OTO reactor, and an inner surface forming a conduit for delivering the feed from the first end to the second end and into the OTO reactor.

In yet another embodiment, the invention relates to an improved process for producing light-olefins from an oxygenate-containing feedstock comprising contacting the feedstock in an OTO reactor with a OTO catalyst under conditions effective to form an effluent comprising the light olefins, the improvement comprising: contacting the feedstock upstream of the OTO reactor with a metal-containing catalyst comprising one or more metals from Groups 2, 3, and 4 of the Periodic Table and/or one or more metals in the Lanthanide and Actinide series. The improvement results in an OTO catalyst lifetime increase of at least about 10%.

BRIEF DESCRIPTION OF THE DRAWINGS

This invention will be better understood by reference to the Detailed Description of the Invention when taken together with the attached drawing.

DETAILED DESCRIPTION OF THE INVENTION

Figure 1:
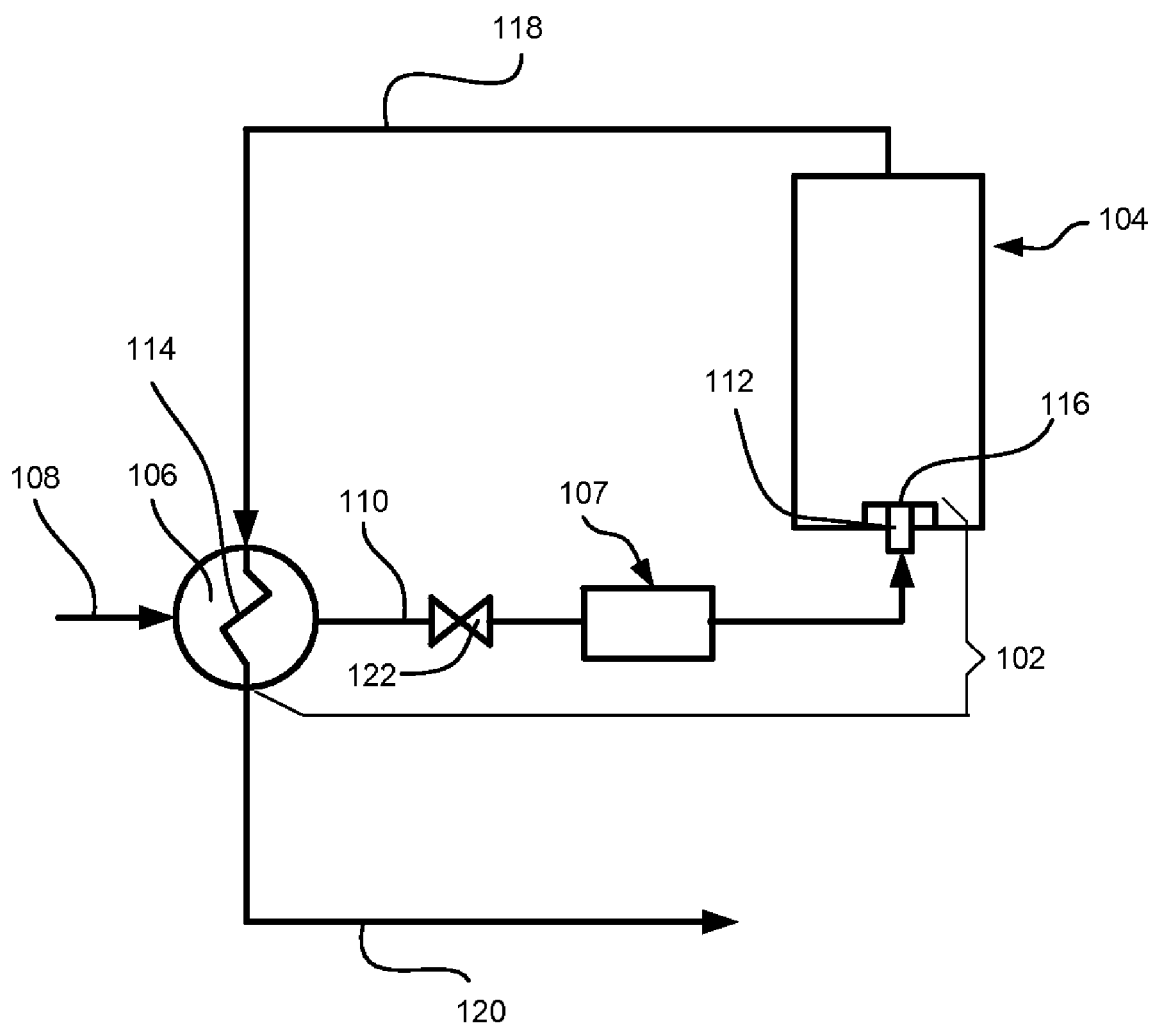
FIG. 1 illustrates a flow diagram of a methanol to olefin reactor system including the Feed Vaporization and Introduction ("FVI") system and the MTO reactor.

The invention is based in part on the discovery that oxygenate decomposition products, such as those that can form when an oxygenate feed is heated prior to its introduction into an OTO reaction zone, can degrade the performance of the OTO catalyst. Accordingly, it has been discovered that the production of catalyst coke, methane, and undesirable OTO reaction byproducts can be diminished by contacting the oxygenate feed with a catalytically effective amount of a catalyst comprising at least one metal selected from Groups 2, 3, and 4 of the Periodic Table under catalytic conversion conditions before introducing the feed into the OTO reactor. The effect is more pronounced with small-pore molecular sieve OTO catalysts (e.g., HZSM-5) than with medium or large-pore molecular sieve OTO catalysts. The term "Periodic Table" as used herein means the Periodic Table of the Elements as published in THE MERCK INDEX, Twelfth Edition, Merck & Co., Inc. 1996. The catalyst comprising at least one metal selected from Groups 2, 3, and 4 of the Periodic Table can be referred to as the "first" catalyst, to distinguish that catalyst from the OTO catalyst in the OTO reactor which can be referred to as the "second" catalyst.

In an embodiment, the invention is directed to reducing the amount of feed decomposition byproducts such as metal-catalyzed side reaction byproducts in reactor systems, and in particular, in methanol to olefin (MTO) reactor systems. When a feedstock including an oxygenate such as methanol contacts a metal surface, e.g., the OTO reactor walls, at relatively high temperatures and pressures, the oxygenate decomposes to form the undesirable byproducts. In addition to metal-catalyzed side reactions occurring on reactor walls, metal catalyzed side reactions may occur before the feedstock enters the reactor. Thus in one embodiment, the invention relates to a process for producing light olefins that includes the conversion of undesirable byproducts formed, e.g., in metal catalyzed side reactions in the feed vaporization and introduction (FVI) system, into less harmful species, e.g., species that are not as effective for deactivating the OTO catalyst. The FVI system is typically the region of the reactor system beginning at the point that at least a portion of the feedstock is in a vaporized state and extending to the point that the feedstock exits the feed introduction nozzle and enters the OTO reactor where the feedstock contacts the OTO catalyst (the second catalyst). As the resulting light olefin stream contains fewer metal-catalyzed side reaction byproducts than is produced in conventional OTO reactor systems, olefin separation and purification costs can be reduced. Moreover, since the metal-catalyzed side reaction byproducts decrease OTO catalyst performance, diminishing the production of such byproducts results in an increase in OTO catalyst lifetime, which can result in a desirable increase in olefin yield. The olefins produced by the OTO reaction are particularly suitable for use as a feed in the manufacture of polyolefins.

In one embodiment, the invention involves contacting the feed with the first catalyst in the FVI system. In an upstream region of the FVI system, the feedstock is at least partially vaporized by one or more heating device(s). Optionally, the heating results in the production of a feed that is substantially all in the vapor state. Following the heating, the at least partially-vaporized feed contacts the first catalyst, generally in a bed (or "guard bed"). Finally, the feed is conducted away from the guard bed downstream through feed line(s) to one or more feed introduction means for introducing the at least partially vaporized feed into the OTO reactor. The feed introduction means can be any means capable of introducing the feed into the OTO reactor for contact with the OTO catalyst under catalytic conversion conditions in a fixed-bed configuration, a fluidized bed configuration, or combinations thereof. Optionally, feed injector nozzles can be used. Optionally, the inner surface of at least a portion of the FVI system is formed of metal which absorbs heat from the reactor volume thereby creating conditions in the FVI system conducive to the formation of metal catalyzed side reaction byproducts. As used herein, the term "inner surface" is defined to mean a portion of the FVI system, e.g., the feed introduction nozzle, which contacts the feedstock prior to its introduction into the OTO reaction unit. Thus, in one embodiment the invention is directed to a method for making an olefin-containing product from an oxygenate-containing feedstock including directing the feedstock through a feed introduction nozzle having an inner surface, the nozzle being attached to an OTO reactor, such as a MTO reactor. Optionally, the nozzle is maintained at conditions effective to produce less than 0.8 wt. %, e.g., less than 0.4 wt. % of metal catalyzed side reaction byproducts, excluding CO, $CO_2$ and $H_2$, based on the total weight of the feedstock. Optionally, the conditions are effective to substantially eliminate the formation of metal catalyzed side reaction byproducts in the feed introduction nozzle. In the reactor, the feedstock contacts a catalyst under conditions effective to form an effluent comprising light olefins.

The invention provides a method for making an olefin product from an oxygenate-containing feedstock while reducing the amount of feed-decomposition byproducts introduced into the OTO reactor from the FVI system. Such feed decomposition byproducts can reduce the useful life of the OTO catalyst by prematurely deactivating the catalyst's molecular sieve species. While not wishing to be bound by any theory or model, it is believed that at least some of the feed decomposition byproducts function as catalyst deactivating agents (e.g., coke precursors), which facilitate the formation of coke in the OTO catalyst cage structure, which would otherwise be more active for the catalytic production of light olefin.

Catalyst additives have been disclosed to overcome the problem of catalyst deactivation from, e.g., coke formation. For example, the publication *Effects of decrease in number of acid sites located on the external surface of* Ni-SAPO-34 *crystalline catalyst by the mechanochemical method*, Catalysis Letters 53, pp. 171-176 (1998) discloses that coke formation can be mitigated in the conversion of methanol to ethylene over Ni-SAPO-34 by milling the catalyst with MgO, CaO, BaO or $Cs_2O$ on microspherical non-porous silica. In one embodiment, BaO is used. The combination of MTO catalyst with a catalytically active metal has also been disclosed in International Publication No. WO 98/29370, which discloses the conversion of oxygenates to olefins over a small pore non-zeolitic molecular sieve containing a metal selected from the group consisting of a lanthanide, an actinide, scandium, yttrium, a Group 4 metal, a Group 5 metal or combinations thereof. While these references deal with coke and coke precursors formed in the OTO reaction, it has been discovered that it is efficient to remove or prevent the formation of coke precursors upstream of the OTO reactor.

As the feedstock passes through the FVI system, the oxygenate contacts the means for heating the feedstock. The feedstock is generally heated until at least a portion of the feedstock is in the vapor phase. The heating means can be, e.g., heating devices such as one or more tube furnaces or heat exchangers, where the feedstock is conducted in contact with an inner surface (generally metallic) of one or more of the heating device(s). Downstream of the heating means, the FVI system comprises the feed introduction means (e.g., at least one feed nozzle), and/or the lines connecting the heat exchanger(s) to the feed introduction nozzle. In one side-reaction in the FVI system, the metal surface of the heat exchanger(s), line(s) and/or feed introduction nozzle act as a catalyst at high temperatures and convert some of the methanol in the feedstock to hydrogen, carbon monoxide, carbon dioxide, methane and/or graphite.

In order to diminish or substantially eliminate the amount of catalyst deactivation precursors produced by the FVI system and introduced into the OTO reactor, means are provided for the feed to contact a metal-containing catalyst downstream of the feed-heating means but upstream of the feed introduction means. The metal-containing catalyst can comprise one or more metals from Groups 2, 3, and 4 of the Periodic Table and/or one or more metal in the Lanthanide and Actinide series. The metals are generally in the form of a metal oxide, and can be, e.g., non-acid or basic metal oxides.

In an embodiment, one metal oxide catalyst is used, and in another embodiment, two or more metal oxide catalysts are used together. When two or more metal oxide catalysts are used, the catalysts can be produced together, or produced separately and then combined. In an embodiment where the metal oxides are each made separately and then contacted together, the catalysts can be mixed together in a slurry or hydrated state or in a substantially dry or dried state, e.g., the metal oxides can be contacted in a hydrated state.

The method selected for producing the metal oxide catalysts of the invention is not critical, and conventional methods can be used. For example, the metal oxide can be made from metal oxide precursors, such as metal salts. Other suitable sources of the metal oxides can include compounds that form these metal oxides during calcination, such as oxychlorides and nitrates. Alkoxides are also sources of the metal oxides of the invention, for example yttrium n-propoxide. Suitable methods for producing the metal oxide catalysts are described in U.S. Pat. Nos. 6,844,291, 7,205,447, and 6,906,232, which are incorporated by reference herein in their entirety. It should be noted however, that the catalysts of these references are described for use in combination with a molecular sieve OTO catalyst for use in an OTO reactor or for treating an olefin stream, which is different from the present invention which uses such catalyst e.g., as a guard bed upstream of the OTO reactor.

In one embodiment, at least one Group 2, 3, or 4 metal oxide or oxide of the Lanthanide and/or Actinide series is hydrothermally treated under conditions that include a temperature of at least 80° C., e.g., at least 100° C. The hydrothermal treatment can take place, e.g., in a sealed vessel at greater than atmospheric pressure, or in an open vessel under reflux conditions. Agitation of the selected metal oxide or oxides series in the liquid medium, for example, by the action of refluxing liquid and/or stirring, can promote the effective interaction of the oxide with the liquid medium. Typically, the duration of the contact of the oxide or oxides with the liquid medium is not critical, and can be, e.g., at least 1 hour, or at least 8 hours. The liquid medium for this treatment is generally not critical, and can be, e.g., a liquid having a pH of about 7 or greater, or 9 or greater. Non-limiting examples of suitable liquid media include water, hydroxide solutions (including hydroxides of NH4+, Na+, K+, Mg2+, and Ca2+), carbonate and bicarbonate solutions (including carbonates and bicarbonates of NH4+, Na+, K+, Mg2+, and Ca2+), pyridine and its derivatives, alkyl/hydroxylamines, and combinations and/or reaction products thereof.

In yet another embodiment, the Group 2, 3, and/or 4 metal oxide and/or or the oxide of the Lanthanide and/or Actinide series can be prepared, for example, by first preparing a liquid solution comprising a source of a metal or combination of metals (including the lanthanide(s) and/or actinide(s), which for the purpose of this description will be considered as metals). Suitable sources for such metals include, but are not limited to, salts of the selected metal or metals, such as nitrates, sulfates and halides.

This solution containing a source of the selected metal(s) cans then be subjected to conditions sufficient to cause precipitation of the solid metal oxide(s), such as by the addition of a precipitating reagent to the solution. For example, the precipitating agent(s) can be a base such as sodium hydroxide or ammonium hydroxide. Water can be used as a solvent for these solutions. The temperature at which the liquid medium(s) is maintained is generally not critical, and can be, e.g., maintained at less than about 200° C., such as in the range of from about 0° C. to about 200° C. The liquid medium(s) can be maintained at an ambient temperature, for example room temperature (about 20° C. to 25° C.) or the liquid can be cooled or heated. A particular range of temperatures for precipitation is from about 20° C. to about 100° C. The resulting gel can be hydrothermally treated at temperatures of at least 80° C., e.g., at least 100° C. The hydrothermal treatment can take place in a sealed vessel at greater than atmospheric pressure. The gel, in one embodiment, is hydrothermally treated for up to 10 days, e.g. up to 5 days, or up to 3 days. The resulting material can then be recovered, for example by filtration or centrifugation, and washed and dried. The resulting material is optionally then calcined, generally in an oxidizing atmosphere, at a temperature of at least 400° C., e.g., at least 500° C., or from about 600° C. to about 900° C., or from about 600° C. to about 800° C. The calcination time is generally not critical, and can be, e.g., up to 48 hours, or for about 0.5 to 24 hours, such as, for about 1.0 to 10 hours. In an embodiment, the metal oxides catalysts can have a surface area greater than 20 m2/g, can have been calcined to greater than 200° C., and can be capable of converting greater than 25%, e.g., greater than 50%, such as greater than 80% of acetone at room temperature (about 25° C.) in an aldol condensation reaction producing e.g., one or more of diacetone alcohol, mesity oxide, phorone, isophorone, and mesitylene.

In one embodiment, the metal-containing catalyst comprises a molecular sieve and at least one oxide of a metal selected from Group 4 of the Periodic Table of Elements, wherein said metal oxide has an uptake of carbon dioxide at 100° C. of at least 0.03, and typically at least 0.035, mg/m$^2$ of the metal oxide. The metal-containing catalyst can also include (further comprise) at least one of a binder and a matrix material different from said metal oxide. The metal-containing catalyst composition can also include an oxide of a metal selected from Group 2 and/or Group 3 of the Periodic Table of Elements. When used, the Group 4 metal oxide can comprise zirconium oxide. When used, the Group 2 and/or Group 3 metal oxide can comprise one or more oxides selected from calcium oxide, barium oxide, lanthanum oxide, yttrium oxide and scandium oxide. Optionally, the metal-containing catalyst comprises one or more of $Y_2O_3$, $La_2O_3$, $La_2O_3/ZrO_2$, MgO, and CeO.

The metal oxides of the invention are those metal oxides which have an uptake of carbon dioxide at 100° C. of at least 0.03 mg/m$^2$ of the metal oxide, such as at least 0.35 mg/m$^2$. Although the upper limit on the carbon dioxide uptake of the metal oxide is not believed to be critical, in general the metal oxides useful herein will have a carbon dioxide uptake at 100° C. of less than 10 mg/m$^2$ of the metal oxide, such as less than 5 mg/m$^2$.

In order to determine the carbon dioxide uptake of a metal oxide, the following procedure is adopted using a Mettler TGA/SDTA 851 thermogravimetric analysis system under ambient (atmospheric) pressure. A sample of the metal oxide is dehydrated in flowing air to about 500° C. for one about hour. The temperature of the sample is then reduced in flowing helium to about 100° C. After the sample has equilibrated at the desired adsorption temperature in flowing helium, the sample is subjected to 20 separate pulses (about 12 seconds/pulse) of a gaseous mixture comprising 10 wt. % carbon dioxide with the remainder being helium. After each pulse of the adsorbing gas the metal oxide sample is flushed with flowing helium for about 3 minutes. The increase in weight of the sample in terms of mg/mg adsorbent based on the adsorbent weight after treatment at 500° C. is the amount of adsorbed carbon dioxide. The surface area of the sample is measured in accordance with the method of Brunauer, Emmett, and Teller (BET) published as ASTM D 3663 to provide the carbon dioxide uptake in terms of mg carbon dioxide/$m^2$ of the metal oxide.

The invention is compatible with and can be used in combination with conventional methods for diminishing feed decomposition in the feed vaporization and introduction zone of an OTO reaction. Such methods are described, for example, in U.S. Pat. Nos. 6,737,556 and 7,034,196 both of which are incorporated by reference herein in their entirety.

Referring now to the drawing, FIG. 1 illustrates an MTO reactor system in accordance with one embodiment. The MTO reactor system includes a feedstock vaporization and introduction system, or FVI system, which is generally designated by numeral 102, and an MTO reactor, which is generally designated by numeral 104. As defined herein, the FVI system 102 is a region of the reactor system beginning at the point that at least a portion of the feedstock is in a vaporized state and extending to the point that the feedstock exits the feed introduction means and enters the MTO reactor, as illustrated in FIG. 1. At least a portion of the FVI system may be formed of one or more metals, or an alloy of metals, e.g., steel, to accommodate the temperature and pressure of the feedstock as it is transported to the reactor. For example, at least a portion of the FVI system comprises at least one stainless steel alloy selected from the group consisting of 410, 304, 316, 400, 330, 800, 600, 825, 601, 625, 617, 956, 693, and 671.

In FIG. 1, a liquid oxygenate feedstock or feed stream 108 containing an oxygenate such as methanol is shown being directed to heating device(s) 106 (such as one or more heat exchangers, e.g., a transfer line heat exchanger) which heats the feedstock. The feedstock can be heated to a temperature that is below, at, or above the feedstock's bubble point under process conditions, e.g., a temperature just below the feedstock's bubble point. Optionally, a series of heating devices can be used to gradually heat the feedstock in steps, as disclosed in U.S. Pat. No. 6,121,504, which is incorporated herein by reference in its entirety. If a series of heating devices is implemented in the present invention, a series of lines can be used to transfer the feedstock between the heating devices to the feed introduction nozzle. The lines can be formed of a convenient material, e.g., a metal or alloy such as steel to accommodate the temperature and pressure of the feedstock. When certain metals and metal alloys are used, they can undesirably catalyze side reactions of the feedstock resulting in the formation of coke precursors.

In an embodiment, the heating device is a shell and tube heat exchanger. The heating medium may be all or a portion of the product effluent 118 of the MTO reactor, as shown in FIG. 1, a heat integration stream, e.g., from a water stripper or quench tower, or any other material having a higher temperature than the feedstock. For example, the heating means 106 can cause at least a portion of the feedstock stream to vaporize. In an embodiment where a portion of the feedstock vaporizes, the point at which at least a portion of the feedstock vaporizes is defined herein as the FVI system inlet 114. Optionally, the FVI inlet is within the heating device 106.

After being heated in the heating device(s) 106, the heated feedstock is conducted through line(s) 110 to a region 107 where the heated feedstock is exposed to the first catalyst under catalytic conversion conditions to diminish the amount of OTO-catalyst deactivating agents (e.g., coke precursors) in the heated feedstock before the heated feedstock is introduced into the OTO reactor. Process conditions in this region 107, which can be, e.g., in the form of a guard bed, can include the following: average temperature of region 107 can be the range of 200° C. to 700° C., such as 300° C. to 600° C.; average pressure can be in the range of 5 kpaa to 5 MPaa, such as 50 kpaa to 0.5 MPaa, and WHSV can be in the range of 1 to 10,000, such as 100 to 1000. Optionally, the average temperature in region 107 is the same or lower than the average temperature in the OTO reactor. Optionally, the pressure in region 107 can be approximately the same as (or slightly higher than) the pressure in the OTO reactor. In an embodiment, region 107 comprises a fixed bed of the catalyst.

Following contact with the first catalyst, the feed can be conducted through line(s) 110 to a feed introduction nozzle 112. The feed introduction nozzle may be formed of a metal or alloy such as steel and may protrude into the MTO reactor volume. Alternatively, the portion of the nozzle adjacent the reactor may be oriented flush with the interior surface of the reactor wall. The heated feedstock can pass through the feed introduction nozzle 112 and enters the MTO reactor 104.

The pressure in the MTO reactor may be less than the pressure of the feedstock within the FVI system, and the temperature within the MTO reactor may be much higher than the temperature in the FVI system. Accordingly, a portion or the entirety of any liquid contained in the heated feedstock may vaporize as it exits the feed introduction nozzle at 116 and enters the MTO reactor. The FVI system outlet is defined as the point where the feedstock enters the feed introduction means 112.

In the MTO reactor 104, the oxygenates (e.g., methanol) in the feed stream contacts a catalyst under conditions effective to form an olefin product which exits the reactor in product effluent 118. As indicated above, the product effluent 118 from the MTO reactor 104 may be directed to the heat exchanger(s) 106 in order to heat the feed stream 108. As shown in FIG. 1, after the product effluent 118 has heated the feed stream 108, it may be directed in line 120 to a product separation and purification system (not shown). Alternatively, the product effluent may be directed to the product separation and purification system, optionally without first being directed to a heat exchanger.

In one embodiment, the feedstock is maintained at a temperature effective to diminish or eliminate the formation of metal-catalyzed side reaction byproducts. In this embodiment, the feedstock may act as a cooling agent for cooling the inner metal surface of one or more of the following: at least a portion of the heating device(s), at least a portion of the line(s), and/or at least a portion of the feed introduction means. The desired temperature of the feedstock throughout the FVI system is optionally ≦about 400° C., e.g., ≦about 350° C., such as ≦about 300° C., or ≦about 250° C., or ≦about 200° C., or ≦150° C., e.g., in the range of about 25° C. to 150° C. These relatively low temperatures may be maintained by controlling the heating characteristics and number of the feedstock heating device(s), and/or by insulating and/or cooling one or more of the following: at least a portion of the heating device(s), at least a portion of the line(s), and/or at least a portion of the feed introduction means, as discussed in more detail below. One effective FVI system produces vapor feed at its saturation, or dew point. In such an FVI system the pressure at which vaporization occurs will usually determine the temperature. Superheating of the vapor can then be introduced by reducing the pressure of the saturated vapor feedstock either within or prior to entering the feed nozzle. Surprisingly and unexpectedly, it has been found that the introduction of a low temperature feedstock into a hot MTO reactor does not substantially affect (e.g., substantially reduce) the formation of light olefins in the MTO reactor. Such methods are described in U.S. Pat. No. 7,034,196, for example.

Additionally or alternatively, the method can include maintaining at least a portion of the inner surfaces of the feed vaporization and introduction system, e.g., the inner surface of the feed introduction nozzle, at a temperature effective to reduce or eliminate the formation of metal catalyzed side reaction byproducts. In accordance with the present invention, the temperature of the metal-containing inner surface(s) of the FVI system and/or the feed introduction means can be maintained at the desired temperature in a variety of ways. For example, one or more of the heating device(s), the line(s) between the feed heating device(s) and the feed introduction means, and/or the feed introduction means itself may be jacketed with a thermally insulating material. Additionally or alternatively, one or more of the heating device(s), the line(s) between the feed heating device(s) and the feed introduction means, and/or the feed introduction means itself may include a cooling device for controlling the temperature of all or a portion of the FVI system and/or the feed introduction means. The scope of the invention also includes temperature monitoring and/or controlling means for regulating the temperature of the FVI and/or feed introduction means. Optionally, the feed introduction means can incorporate a jacket formed of a thermally insulating material and/or a cooling system. Optionally, the jacketing and cooling embodiments and the embodiment using a low temperature feedstock can be combined. Such methods are described in U.S. Pat. No. 7,034, 196, for example.

The invention is also compatible with, and can be used in combination with, FVI systems comprising an alloy resistant to the formation of metal catalyzed side reaction byproducts. Optionally, the alloy can be resistant to carburization and metal dusting. See, e.g., Paper No. 02394 entitled *Nickel-Base Material Solutions to Metal Dusting Problems* from the Corrosion 2002 Conference (NACE International), which is incorporated herein by reference. Such an FVI system is described in U.S. Pat. No. 6,737,556, which is incorporated by reference herein in its entirety.

The heated feedstock from the FVI system can be introduced into the MTO reactor as shown in FIG. 1. Conditions in the MTO reactor including the pressure, temperature, weight hourly space velocity (WHSV), etc., are generally selected to be conducive to converting the methanol to light olefins, as discussed in more detail below. At least a portion of the FVI system, and/or the feed introduction nozzle, can be beneficially monitored and/or maintained at conditions, e.g., temperatures and/or pressures, effective to reduce, minimize or substantially eliminate the formation of metal catalyzed side-reaction byproducts generally irrespective of the conditions within the MTO reactor. That is, the conditions within the MTO reactor may or may not be conducive to the formation of metal catalyzed side-reaction byproducts. Thus, the invention is compatible with and can be implemented with a deactivated or passivated reactor.

Typically, molecular sieve catalysts have been used to convert oxygenate compounds to light olefins. Silicoaluminophosphate (SAPO) molecular sieve catalysts are particularly desirable in such a conversion process, because they are highly selective in the formation of ethylene and propylene.

The feedstock optionally contains one or more aliphatic-containing compounds that include alcohols, amines, carbonyl compounds for example aldehydes, ketones and carboxylic acids, ethers, halides, mercaptans, sulfides, and the like, and mixtures thereof. The aliphatic moiety of the aliphatic-containing compounds typically contains from 1 to about 50 carbon atoms, optionally from 1 to 20 carbon atoms, more such as from 1 to 10 carbon atoms, e.g., from 1 to 4 carbon atoms.

Non-limiting examples of aliphatic-containing compounds include: alcohols such as methanol and ethanol, alkyl-mercaptans such as methyl mercaptan and ethyl mercaptan, alkyl-sulfides such as methyl sulfide, alkyl-amines such as methyl amine, alkyl-ethers such as dimethyl ether, diethyl ether and methylethyl ether, alkyl-halides such as methyl chloride and ethyl chloride, alkyl ketones such as dimethyl ketone (acetone), aldehydes such as formaldehydes, and various organic acids such as acetic acid.

In one embodiment, the feedstock contains one or more oxygenates, more specifically, one or more organic compound(s) containing at least one oxygen atom. Optionally, the oxygenate in the feedstock comprises or is one or more alcohol(s), optionally aliphatic alcohol(s) where the aliphatic moiety of the alcohol(s) has from 1 to 20 carbon atoms, optionally from 1 to 10 carbon atoms, and such as from 1 to 4 carbon atoms. The alcohols useful as feedstock in the process of the invention include lower straight and branched chain aliphatic alcohols and their unsaturated counterparts. Non-limiting examples of oxygenates include methanol, ethanol, n-propanol, isopropanol, methyl ethyl ether, dimethyl ether, n-propanol, isopropanol, methyl ethyl ether, dimethyl ether, diethyl ether, di-isopropyl ether, formaldehyde, dimethyl carbonate, dimethyl ketone, acetic acid, and mixtures thereof. In one embodiment, the feedstock is selected from one or more of methanol, ethanol, dimethyl ether, diethyl ether or a combination thereof, e.g., methanol and dimethyl ether, such as predominantly methanol.

The various feedstocks discussed above, particularly a feedstock oxygenate-containing, more particularly a feedstock comprising predominately alcohol, is converted primarily into one or more olefin(s). The olefin(s) or olefin monomer(s) produced from the feedstock can have from 2 to 30 carbon atoms, optionally 2 to 8 carbon atoms, such as 2 to 6 carbon atoms, e.g., 2 to 4 carbons atoms, preferably ethylene an/or propylene.

Non-limiting examples of olefin monomer(s) include ethylene, propylene, butene-1, pentene-1,4-methyl-pentene-1, hexene-1, octene-1 and decene-1, and isomers thereof, such as ethylene, propylene, butene-1, pentene-1,4-methyl-pentene-1, hexene-1, octene-1 and isomers thereof. Other olefin monomer(s) can include unsaturated monomers, diolefins having 4 to 18 carbon atoms, conjugated or non-conjugated dienes, polyenes, vinyl monomers and cyclic olefins.

In one embodiment, the feedstock, optionally of one or more oxygenates, can be converted in the presence of a molecular sieve catalyst composition into olefin(s) having 2 to 6 carbons atoms, such as 2 to 4 carbon atoms. Optionally, the olefin(s), alone or combination, can be converted from a feedstock containing an oxygenate, such as an alcohol, e.g., methanol, to the preferred olefin(s) ethylene and/or propylene.

In one embodiment, the OTO process is a methanol-to-olefins (MTO) process. In an exemplary MTO process, a feedstock comprising predominately oxygenates, such as a methanol-containing feedstock, is converted in the presence of a molecular sieve catalyst composition into one or more olefin(s), such as (predominantly) ethylene and/or propylene, which are often referred to as light olefin(s).

The feedstock, in one embodiment, contains one or more diluent(s), typically used to reduce the concentration of the feedstock. The diluents are generally non-reactive to the feedstock or molecular sieve catalyst composition. Non-limiting examples of diluents can include helium, argon, nitrogen, carbon monoxide, carbon dioxide, water, essentially non-reactive paraffins (especially alkanes such as methane, ethane, and propane), essentially non-reactive aromatic compounds, and mixtures thereof. Optionally, the diluents can be water and nitrogen, e.g., water only. In other embodiments, the feedstock does not contain any diluent.

The diluent can be in the form of a liquid, a vapor, or a combination thereof. The diluent can be, e.g., added directly to a feedstock entering into a reactor or added directly into a reactor, or added with a molecular sieve catalyst composition. In one embodiment, the amount of diluent in the feedstock can be in the range of from about 1 to about 99 mol % based on the total number of moles of the feedstock and diluent, optionally from about 1 to 80 mol %, such as from about 5 to about 50 mol %, e.g., from about 5 to about 25 mol %. In one embodiment, other hydrocarbons are added to a feedstock either directly or indirectly, and include olefin(s), paraffin(s), aromatic(s) (see for example U.S. Pat. No. 4,677,242, addition of aromatics) or mixtures thereof, optionally propylene, butylene, pentylene, and other hydrocarbons having 4 or more carbon atoms, or mixtures thereof.

The process for converting a feedstock, especially a feedstock containing one or more oxygenates, in the presence of a molecular sieve catalyst composition, can be carried out in a reaction process in a reactor, where the process is a fixed bed process, a fluidized bed process (includes a turbulent bed process), optionally a continuous fluidized bed process, such as a continuous high velocity fluidized bed process. The molecular sieve catalyst composition can comprise, e.g., a small-pore molecular sieve, such as a small-pore SAPO molecular sieve. Optionally, the catalyst composition can be selected from among those described in U.S. Pat. No. 6,953,767. For example, the catalyst can comprise silicoaluminophosphate molecular sieves having at least one intergrown phase of molecular sieves having AEI and CHA framework types, the intergrown phase having an AEI/CHA ratio of from about 5/95 to 40/60 as determined by DIFFaX analysis, using the powder X-ray diffraction pattern of a calcined sample of said silicoaluminophosphate molecular sieve.

The reaction processes can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. Nos. 4,076,796 and 6,287,522 (dual riser), and *Fluidization Engineering*, D. Kunii and O. Levenspiel, Robert E. Krieger Publishing Company, New York, N.Y. 1977, which are all herein fully incorporated by reference.

Riser reactors useful in the invention are generally described in *Riser Reactor, Fluidization and Fluid-Particle Systems*, pages 48 to 59, F. A. Zenz and D. F. Othmo, Reinhold Publishing Corporation, New York, 1960, U.S. Pat. No. 6,166,282 (fast-fluidized bed reactor), and U.S. Pat. No. 7,102,050 (multiple riser reactor), which are all herein fully incorporated by reference.

The liquid and vapor feedstocks are optionally the same composition, or contain varying proportions of the same or different feedstock with the same or different diluent.

The conversion temperature employed in the conversion process, specifically within the reactor system, is in the range of from about 200° C. to about 1000° C., optionally from about 250° C. to about 800° C., such as from about 250° C. to about 750° C., or from about 300° C. to about 650° C., or even from about 350° C. to about 600° C., e.g., from about 350° C. to about 550° C.

The conversion pressure employed in the conversion process, specifically within the reactor system, can vary over a wide range including autogenous pressure. The conversion pressure can be based on the partial pressure of the feedstock exclusive of any diluent therein. Optionally, the conversion pressure employed in the process can be in the range of from about 0.1 kPaa to about 5 MPaa, optionally from about 5 kpaa to about 1 MPaa, such as from about 20 kpaa to about 500 kpaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. Optionally, the WHSV is maintained at a level sufficient to keep the catalyst composition in a fluidized state within a reactor.

Typically, the WHSV ranges from about 1 $hr^{-1}$ to about 5000 $hr^{-1}$, optionally from about 2 $hr^{-1}$ to about 3000 $hr^{-1}$, such as from about 5 $hr^{-1}$ to about 1500 $hr^{-1}$, e.g., from about 10 $hr^{-1}$ to about 1000 $hr^{-1}$. In one embodiment, the WHSV can be greater than 20 $hr^{-1}$; optionally the WHSV for conversion of a feedstock containing methanol, dimethyl ether, or both, can be in the range of from about 20 $hr^{-1}$ to about 300 $hr^{-1}$.

The superficial gas velocity (SGV) of the feedstock including diluent and reaction products within the reactor system is optionally sufficient to fluidize the molecular sieve catalyst composition within a reaction zone in the reactor. The SGV in the process, particularly within the reactor system, more particularly within the riser reactor(s), is at least 0.1 meter per second (m/sec), optionally greater than 0.5 m/sec, e.g., greater than 1 m/sec, such as greater than 2 m/sec, e.g., greater than 3 m/sec, or greater than 4 m/sec. See for example U.S. Pat. No. 6,552,640, which is incorporated by reference in its entirety.

All patents, test procedures, and other documents cited herein, including priority documents, are fully incorporated by reference to the extent such disclosure is not inconsistent and for all jurisdictions in which such incorporation is permitted.

While the illustrative forms disclosed herein have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside herein, including all features which would be treated as equivalents thereof by those skilled in the art to which this disclosure pertains.

When numerical lower limits and numerical upper limits are listed herein, ranges from any lower limit to any upper limit are contemplated.

EXAMPLE

In order to provide a better understanding of the present invention including representative advantages thereof, the following example is offered. The example compares the reactivity of a methanol feedstock in a stainless steel reactor with a methanol feedstock in a coated reactor at various temperatures. This example illustrates the concept of adding a reactive pre- (or guard-) bed of metal oxide (MO) catalyst before (i.e., upstream of where) the preheated methanol is introduced into the reactive section containing the MTO catalyst. Experiments are carried out in a laboratory testing unit at 25 psig (172 kpag) using approximately 19 mg of a SAPO molecular sieve and neat MeOH as the feed at a WHSV of 100 hr$^{-1}$. The SAPO molecular sieve of the MTO catalyst is made in accordance with the process described in U.S. Pat. No. 6,953,767.

The methanol feed flows first to a vaporizer/preheat zone, is transported via a heated tube, and is then further heated in a heating region to approach reaction temperatures. The heating region is silicon-coated to minimize any MeOH decomposition. The heated methanol is then contacted with a bed of the MTO catalyst. MTO reactions take place in the catalyst bed and the product stream passes out of the reactor; a portion of the product stream is captured in one or more sample loops for analysis which provide the basis for calculating catalyst performance.

Table 1 illustrates the basis of the invention with respect to a first set of reference cases (the first three lines of Table 1), a second set of reference cases (samples 1-3) in which the reactor vessel has a silica coating and the invention (Table 1, examples 4-6) in which a pre-bed of yttrium oxide is used between methanol vaporization and contact of the pre-heated methanol with the MTO catalyst in the reactor vessel. The methanol feed is contacted with the yttrium oxide after the methanol feed is both (i) vaporized and (ii) preheated to near reaction temperature. This zone is nominally at the same temperature as the reactive zone, i.e., about 500° C. in these experiments.

In Table 1 selectivities are given as run averages (i.e., selectivities are calculated based on integration over the run from freshly charged MTO catalyst to deactivated MTO catalyst). Lifetime is defined as the amount of methanol converted (grams)/the amount of molecular sieve charged (grams). POR is the weight ratio of C2= to C3=.

As can be seen in Table 1, a plain stainless steel reactor tube yields an average lifetime upon testing of 18.4 grams methanol converted/gram of molecular sieve catalyst. As comparative samples 1-3 illustrate, coating the stainless steel tube with silica (i.e., "silica steel") increases MTO catalyst life to 23.4 g/g. However, as may be seen from examples 4-6, when the methanol feed contacts the yttria catalyst upstream of the silica steel reactor the lifetime of the MTO catalyst is further increased to 34.4 g/g (an 86% increase over the base stainless steel-alone case and 47% higher than the silica steel case). Higher lifetimes are generally desirable since they will require less regeneration of MTO catalyst and in general result from forming less undesirable coke.

As a further example, a second series of cases is carried out and the results are presented in Table 2. These cases illustrate the effect of lowering the temperature of the bed of yttria catalyst and the impact of higher and lower WHSV based on the yttria catalyst charge and feed rate. Note that two WHSVs are used in these cases: (1) a WHSV based on the weight of active MTO catalyst (held constant in these experiments at 100 hr$^{-1}$, and (2) a WHSV based on the mass of the yttria catalyst (defined as WHSV$_{prebed}$). WHSV$_{prebed}$ is varied between ~200 and 1000 hr$^{-1}$ in the cases, while the WHSV for the MTO reaction is held at about 100. For all of the samples in Table 2 the pressure is fixed at 25 psig. As shown in samples 7 and 8 of table 2, when a thin bed of iron filings is used at the reactor inlet to provide additional surface area to facilitate the decomposition of methanol, there is a resulting decrease in the lifetime of the MTO catalyst by about 38% over the reference cases shown in Table 2. In other words, the effects caused by feed decomposition are deliberately enhanced in samples 7 and 8.

In Table 2, samples 9-14, a thin prebed of yttria metal oxide (ranging from approximately 1.9 mg to 9.5 mg to yield WHSV$_{prebed}$ values of approximately 200, 333, and 1,000 hr$^{-1}$) is added just upstream of the active MTO catalyst, and the temperature of the prebed is lowered to approximately 350° C. to evaluate the performance at a lower prebed temperature. Samples 9-14 in Table 2 illustrate desirable increases in lifetime (increases in the range of from 8-16%, e.g., about 10%) that are found even at the highest WHSV$_{prebed}$ over the reference cases in Table 2 with no prebed of yttria. No significant change in lifetime improvement is observed when the yttria catalyst charge is increased from 1.9 mg to 5.7 mg and finally to 9.6 mg (corresponding to WHSV values of approximately 1000, 333 and 200 respectively, based on the weight of the yttria and the methanol feed rate).

TABLE 1

| | Description | Run No. | T | WHSV | $C_1$ | $C_2^-$ | $C_3^-$ | $C_3^\circ$ | $C_4^-$ | $C_5^+$ | POS | Lifetime | POR | C6-C9 |
|---|---|---|---|---|---|---|---|---|---|---|---|---|---|---|
| Reference | SS tube | 20249 | 500 | 101 | 2.3% | 39.0% | 38.3% | 0.6% | 11.5% | 4.8% | 77.3% | 19.13 | 1.02 | 1.69% |
| Reference | SS tube | 20250 | 500 | 102 | 2.2% | 38.4% | 38.5% | 0.7% | 11.6% | 5.1% | 76.9% | 18.11 | 1.00 | 1.84% |
| Reference | SS tube | 20251 | 500 | 103 | 2.0% | 38.2% | 38.8% | 0.7% | 11.8% | 5.1% | 77.1% | 18.01 | 0.99 | 1.84% |
| 1 | Si Coated SS tube | 20140 | 500 | 98 | 1.3% | 35.8% | 41.2% | 0.6% | 13.7% | 4.8% | 77.0% | 23.59 | 0.87 | 1.62% |
| 2 | Si Coated SS tube | 20141 | 500 | 102 | 1.3% | 35.7% | 41.3% | 0.6% | 13.7% | 4.8% | 77.0% | 23.30 | 0.86 | 1.57% |
| 3 | Si Coated SS tube | 20142 | 500 | 100 | 1.4% | 36.7% | 40.6% | 0.6% | 13.3% | 4.8% | 77.3% | 23.42 | 0.90 | 1.63% |
| 4 | $Y_2O_3$ Prebed | 20222 | 500 | 101 | 1.6% | 35.5% | 40.9% | 0.6% | 13.2% | 6.8% | 76.4% | 35.90 | 0.87 | 2.67% |
| 5 | $Y_2O_3$ Prebed | 20223 | 500 | 104 | 1.7% | 35.7% | 41.1% | 0.5% | 13.2% | 6.3% | 76.8% | 33.92 | 0.87 | 2.41% |
| 6 | $Y_2O_3$ Prebed | 20224 | 500 | 101 | 1.7% | 36.1% | 40.8% | 0.6% | 13.0% | 6.3% | 77.0% | 33.45 | 0.89 | 2.38% |

TABLE 2

| | Description | Run No. | T | WHSV | $C_1$ | $C_2^-$ | $C_3^-$ | $C_3^\circ$ | $C_4^-$ | $C_5^+$ | POS | Lifetime | POR | C6-C9 |
|---|---|---|---|---|---|---|---|---|---|---|---|---|---|---|
| Reference | Si Coated SS tube | 20338 | 475 | 103 | 1.5% | 37.8% | 39.2% | 0.6% | 12.8% | 5.5% | 77.0% | 26.66 | 0.96 | 1.83% |

TABLE 2-continued

| | Description | Run No. | T | WHSV | $C_1$ | $C_2^=$ | $C_3^=$ | $C_3^°$ | $C_4^=$ | $C_5^+$ | POS | Lifetime | POR | C6-C9 |
|---|---|---|---|---|---|---|---|---|---|---|---|---|---|---|
| Reference | Si Coated SS tube | 20339 | 475 | 104 | 1.6% | 38.9% | 39.3% | 0.5% | 12.3% | 4.7% | 78.1% | 24.25 | 0.99 | 1.93% |
| 7 | 9.6 mg Iron Filings | 20358 | 475 | 98 | 1.2% | 36.5% | 39.0% | 0.9% | 12.9% | 6.5% | 75.5% | 15.61 | 0.94 | 2.13% |
| 8 | 9.6 mg Iron Filings | 20359 | 475 | 105 | 1.2% | 37.3% | 39.0% | 0.8% | 12.7% | 6.0% | 76.3% | 15.86 | 0.96 | 2.11% |
| 9 | 1.9 mg yttria 350° C. | 20319 | 475 | 102 | 1.2% | 34.5% | 40.8% | 0.6% | 13.5% | 6.9% | 75.3% | 29.94 | 0.84 | 1.65% |
| 10 | 1.9 mg yttria 350° C. | 20323 | 475 | 101 | 1.7% | 36.0% | 40.2% | 0.6% | 13.1% | 5.8% | 76.1% | 27.97 | 0.90 | 1.94% |
| 11 | 5.7 mg yttria 350° C. | 20320 | 475 | 102 | 1.5% | 36.0% | 40.3% | 0.6% | 13.2% | 5.8% | 76.3% | 26.62 | 0.89 | 1.82% |
| 12 | 5.7 mg yttria 350° C. | 20324 | 475 | 104 | 1.6% | 36.3% | 40.1% | 0.6% | 13.1% | 5.7% | 76.4% | 28.59 | 0.90 | 1.88% |
| 13 | 9.6 mg yttria 350° C. | 20321 | 475 | 101 | 1.3% | 34.9% | 40.7% | 0.6% | 13.5% | 6.5% | 75.6% | 28.65 | 0.86 | 1.70% |
| 14 | 9.6 mg yttria 350° C. | 20325 | 475 | 103 | 2.5% | 37.2% | 39.2% | 0.5% | 12.4% | 5.0% | 76.4% | 30.53 | 0.95 | 2.47% |

Having now fully described the invention, it will be appreciated by those skilled in the art that the invention can be performed within a wide range of parameters within what is claimed, without departing from the spirit and scope of the invention.

What is claimed is:

1. A method for forming olefins from an oxygenate-containing feedstock, comprising:
   contacting the feedstock comprising oxygenates with a first catalyst upstream of an OTO reactor, the first catalyst consisting of a reactive guard bed of metal oxides of one or more metals from Groups 2, 3, and 4 of the Periodic Table and one or more metals in the Lanthanide and Actinide series; and then
   contacting the feedstock in the OTO reactor with a second catalyst under conditions effective to form an effluent comprising the olefins.

2. The method of claim 1, wherein the first catalyst comprises one or more of yttrium, lanthanum, magnesium, and zirconium.

3. The method of claim 1, wherein the first catalyst is an oxide of yttrium, lanthanum, magnesium, or zirconium, or a combination thereof.

4. The method of claim 1, wherein the first catalyst is yttrium oxide.

5. The method of claim 1, further comprising vaporizing at least a portion of the feedstock before contacting the first catalyst.

6. The method of claim 1, wherein the feedstock is introduced into the OTO reactor through a feed introduction nozzle, the feed introduction nozzle comprising an inner surface in contact with the feedstock, wherein the inner surface comprises a first material resistant to the formation of metal-catalyzed side reactions.

7. The method of claim 6, wherein the inner surface comprises a coating layer, the coating layer being formed, at least in part, of the first material.

8. The method of claim 6, wherein the first material is at least one stainless steel alloy selected from the group consisting of 410, 304, 316, 400, 330, 800, 600, 825, 601, 625, 617, 956, 693, and 671.

9. The method of claim 6, further comprising maintaining the feedstock below 400° C. while the feedstock is in the nozzle by one or more of:
   (i) cooling at least a portion of the inner surface of the nozzle with a cooling system, or
   (ii) jacketing the nozzle with a thermally insulating material.

10. The method of claim 6, further comprising:
    maintaining the nozzle at conditions effective to produce less than 0.8 weight percent of metal catalyzed side reaction byproducts excluding CO, $CO_2$ and $H_2$.

11. The method of claim 1, wherein the feedstock is in the vapor state when contacting the first catalyst.

12. The method of claim 1, wherein the feedstock is exposed to a temperature in the range of 200° C. to 700° C. at a pressure in the range of 5 kPaa to 5 MPaa, with a WHSV in the range of 1 to 10,000 when in contact with the first catalyst, and wherein the feedstock is exposed to a temperature in the range of 200° C. to 1,000° C. at a pressure in the range of 0.1 kPaa to 5 MPaa, with a WHSV in the range of 1 to 5,000 when in contact with the second catalyst.

13. The method of claim 1, wherein the feedstock in contact with the first catalyst is exposed to a temperature that is ≦ the temperature to which the feedstock is exposed in contact with the second catalyst.

14. The method of claim 1, wherein at least a portion of the first catalyst is located in a fixed bed.

15. The method of claim 1, wherein at least a portion of the second catalyst is located in a fluidized bed.

16. The method of claim 15, wherein the fluidized bed is in a riser reactor.

17. In a process for producing olefins from an oxygenate-containing feedstock comprising contacting the feedstock in an OTO reactor with an OTO catalyst under conditions effective to form an effluent comprising the olefins, the improvement comprising: contacting the feedstock comprising oxygenates upstream of the OTO reactor with a metal-containing catalyst consisting of a reactive guard bed of metal oxides of one or more metals from Groups 2, 3, and 4 of the Periodic Table and one or more metals in the Lanthanide and Actinide series.

18. The method of claim 17 wherein the improvement results in an OTO catalyst lifetime increase of at least 10%.

19. The method of claim 17, wherein at least a portion of the metal-containing catalyst is located in a fixed bed.

20. The method of claim 17, wherein the OTO catalyst comprises small-pore SAPO molecular sieve having an intergrown AEI/CHA framework, and wherein at least a portion of the OTO catalyst is located in a fluidized bed.

* * * * *